(12) United States Patent
Tanaka

(10) Patent No.: US 6,495,517 B2
(45) Date of Patent: Dec. 17, 2002

(54) CYCLOOXYGENASE INHIBITOR

(75) Inventor: Zyunji Tanaka, Tokyo (JP)

(73) Assignee: A. Natterman & Cie. GmbH, Köln (DE)

( * ) Notice: Subject to any disclaimer, the term of this patent is extended or adjusted under 35 U.S.C. 154(b) by 0 days.

(21) Appl. No.: 09/838,125

(22) Filed: Apr. 20, 2001

(65) Prior Publication Data

US 2001/0027176 A1 Oct. 4, 2001

Related U.S. Application Data

(62) Division of application No. 09/344,022, filed on Jun. 25, 1999, now abandoned.

(30) Foreign Application Priority Data

Jul. 1, 1998 (JP) .......................................... 10-186234

(51) Int. Cl.[7] ........................ A61K 38/00; A61K 31/165
(52) U.S. Cl. .......................................... 514/2; 514/617
(58) Field of Search ........................................ 514/2, 617

(56) References Cited

FOREIGN PATENT DOCUMENTS

| DE | 30 27 074 A | 2/1982 |
|---|---|---|
| DE | 36 38 124 A | 5/1988 |
| DE | 195 06 669 A | 8/1996 |
| EP | 0 044 453 A | 1/1982 |
| EP | 0 044 971 A | 2/1982 |
| EP | 0 165 534 A | 12/1985 |
| EP | 0 198 277 A | 10/1986 |
| JP | 01 131113 A | 5/1989 |
| JP | 01 131114 A | 5/1989 |
| JP | 07 233056 A | 5/1995 |
| WO | 97 26968 A | 7/1997 |
| WO | 98 08511 A | 3/1998 |

OTHER PUBLICATIONS

Database Chemabs (Online) Chemical Abstracts Service, Columbus, Ohio, US; Tanaka, Junji et al. "Preparation of organoselenium compounds and lipoxygenase inhibitors containing them," retrieved from STN Database accession No. 124:21817 CA, XP002122515.
Database Chamabs (Online) Chemical Abstracts Service, Columbus, Ohio, US; Tanaka, Amsami et al. "Lipid alterations in spontaneously hyperlipidemic rats (HLR): effects of ebselen on plasma cholesterol, triglycerides and lipoproteins," retrieved from STN Database accession No. 122:71752 CA, XP002123050 & Seo Marianna Ika Daigaku Zasshi (1994), 22 (3), 261–8, 1994.
Database WPI, Section Ch, Week 198927, Derwent Publications Ltd., London, GB; Class A96, AN 1989–195131; XP002122516.
Database WPI, Section Ch, Week 198927, Derwent Pulbications Ltd., London, GB; Class A96, AN 1989–195132; XP002122517.

Shitashige, Miki et al. "Ebselen and sodium selenite, mimics of glutathione peroxidase, inhibit prostaglandin endoperoxide H synthase–1." Japanese Journal of Pharmacology, (1997) vol. 73, No. suppl. 1, pp. 51P. Meeting Info. 70th Annual Meeting of the Japanese Pharmacological Society Chiba, Japan Mar. 22–25, 1997, XP000852811.
Shitashige, M. et al. "Different substrate utilization between prostaglandin endoperoxide H synthase–1 and –2 in NIH3T3 fibroblasts." Biochimica et Biophysica Acta, (Jan. 5, 1998) 1389 (1) 57–66.
Kuhl, P. et al. "Ebselen reduces the formation of LTB in human and procine leukocytes by isomerisation to its 5S, 12R–6–trans–isomer" Prostaglandins, US, Butterworth, Stoneham, MA, Bd. 31, Nr. 6, pp. 1029–1048, XP000654397, ISSN: 0090–6980.
CA 120:315176, Anderson et al., Frei. Radual Bul. Med. 16 (1) (1994).
CA 127:336462, Pluranton, EP 800815 (Oct. 15, 1997).
Pratta, M.A. et al. "Effect of ebselen on IL–1–induced alterations in cartliage metabolism." Inflammation Res. (1998), 47(3), 115–121, 1998, XP000085928.

Primary Examiner—Rebecca Cook
(74) Attorney, Agent, or Firm—Finnegan, Henderson, Farabow, Garrett & Dunner, LLP

(57) ABSTRACT

A cyclooxygenase-2-inhibitor containing as an active ingredient a compound having cyclooxygenase-2-inhibitory activity and exhibiting low toxicity that causes only minor side effects. The active compound is represented by the following formula (1) or (1'):

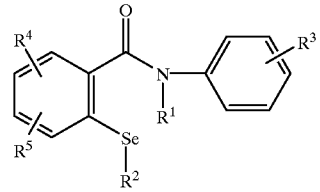

(1)

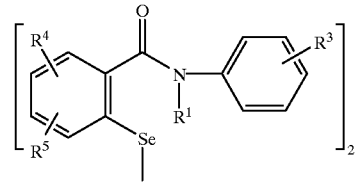

(1')

wherein $R^1$ represents a hydrogen atom or a C1–C3 alkyl group; $R^2$ represents a hydrogen atom, a hydroxyl group, an organic group capable of being bound through its thiol group within the molecule, or $R^1$ and $R^2$ may join to each other to form a single bond; $R^3$ represents a hydrogen atom, a halogen atom, a C1–C3 alkyl group, a C1–C3 alkoxyl group, a trifluoromethyl group, or a nitro group; each of $R^4$ and $R^5$, which may be identical to or different from each other, represents a hydrogen atom, a halogen atom, a C1–C4 alkoxyl group, a trifluoromethyl group, or $R^4$ and $R^5$ may join to each other to form a methylenedioxy group.

6 Claims, No Drawings

CYCLOOXYGENASE INHIBITOR

This is a division of application Ser. No. 09/344,022, filed Jun. 25, 1999 abandoned which incorporated herein by reference.

BACKGROUND OF THE INVENTION

1. Field of the Invention

The present invention relates to a cyclooxygenase-2 inhibitor. The inhibitor inhibits synthesis of prostaglandin H and I, or synthesis of their subsequent metabolites thromboxanes, and can be used as a drug for both treatment and prevention of ischemic diseases, senile dementia, cancer, asthma, arterial sclerosis, and various inflammation diseases.

2. Background Art

Cyclooxygenase (prostaglandin-endoperoxide synthase) is an enzyme that catalyzes in vivo synthesis of prostaglandin H2 from its substrate arachidonic acid. Prostaglandin H2 is physiologically very active. From prostaglandin H2, there are produced metabolites of prostaglandin D2, E2, and F2 and metabolites of thromboxane A2 and B2, all of which are also physiologically very active.

Consequently, inhibition of the cyclooxygenase activity results in inhibition of synthesis of these metabolites. Thus, the prostaglandin H2 inhibitors can inhibit not only prostaglandin H2, but also other physiologically very active compounds, such as prostaglandin D2, E2, and F2 and thromboxane A2 and B2.

Cyclooxygenase is widely known to be involved in inflammation. For treatment of such inflammation, various cyclooxygenase inhibitors have been widely used, including aspirin and indomethacin. However, at the time when these drugs were discovered, there was known only one type of cyclooxygenase that is ubiquitously present in the living body.

Another type of cyclooxygenase; namely, the inducible type of cyclooxygenase, has recently been discovered. This inducible type of cyclooxygenase is induced upon various stimuli and is called cyclooxygenase 2, whereas the ubiquitous type is now called cyclooxygenase 1. Furthermore, it has recently become clear that cyclooxygenase 2 is deeply involved in ischemic diseases, senile dementia, cancer, asthma, arterial sclerosis, and a variety of inflammation diseases. From these observations, cyclooxygenase-2-inhibitors are considered to be potentially very effective drugs for treatment of these diseases (G. Cirino. Biochem. Pharmacol. 55: 105–111, 1998).

SUMMARY OF THE INVENTION

In view of the foregoing, the present invention is to provide a pharmaceutical containing, as an active ingredient thereof, a compound which inhibits cyclooxygenase 2 to thereby serve as an excellent therapeutic drug for the above-mentioned diseases, and which has low toxicity that causes only minor side effects to the extent that they are suitable for clinical use.

Accordingly, the present invention provides the following.

1) A cyclooxygenase-2-inhibitor comprising, as an active ingredient, a compound represented by the following formula (1) or (1'):

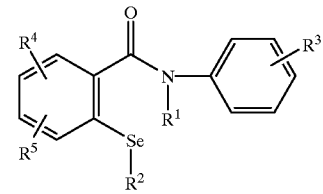

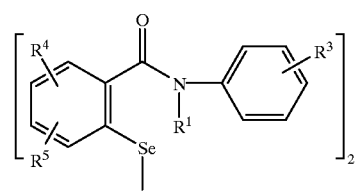

wherein $R^1$ represents a hydrogen atom or an alkyl group having 1–3 carbon atoms; $R^2$ represents a peptide or protein capable of binding through its own thiol group within the molecule, or $R^1$ and $R^2$ may join to each other to form a single bond; and $R^3$ represents a hydrogen atom, a halogen atom, an alkyl group having 1–3 carbon atoms, an alkoxyl group having 1–3 carbon atoms, a trifluoromethyl group, or a nitro group; and each of $R^4$ and $R^5$, which may be identical to or different from each other, represents a hydrogen atom, a halogen atom, an alkoxyl group having 1–4 carbon atoms, a trifluoromethyl group, or $R^4$ and $R^5$ may join to each other to form a methylenedioxy group; a salt thereof, or a hydrate thereof.

2) A cyclooxygenase-2-inhibitor containing, as an active ingredient, 2-phenyl-1,2-benzisoselenazol-3(2H)-one (hereinafter referred to as compound A), a salt thereof, or a hydrate thereof.

3) A cyclooxygenase-2-inhibitor comprising, as an active ingredient, a compound represented by the following formula (2):

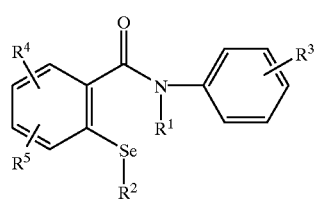

wherein $R^2$ represents a peptide or protein capable of binding through its own thiol group within the molecule, and $R^1$, $R^3$, $R^4$, and $R^5$ are the same as defined above; a salt thereof; or a hydrate thereof.

4) A cyclooxygenase-2-inhibitor containing, as an active ingredient, S-(2-phenylcarbamoyl-phenylselenyl)-albumin (hereinafter referred to as compound B), a salt thereof, or a hydrate thereof.

The present invention is further directed to a method for producing a pharmaceutical composition for the therapy and/or prophylaxis of such diseases which are caused in a disturbance and/or in an influence of the cyclooxygenase-2-inhibition wherein for producing of said composition a cyclooxygenase-2-inhibitor is used as active ingredient, wherein said cyclooxygenase-2-inhibitor is characterized by the before described general formulas.

Moreover the present invention is preferably directed to a method for producing a pharmaceutical composition for the therapy and/or prophylaxis of ischemic diseases, senile dementia, cancer, asthma, arterial sclerosis, and/or inflammation diseases wherein for producing of said composition a cyclooxygenase-2-inhibitor of the afore mentioned type is used as active ingredient.

In the frame of the present invention the term active ingredient is not only used for a single active ingredient but also for a mixture of active ingredients, which are used for the producing of the inventive composition accordingly.

Furthermore the present invention is directed to a method for therapy and/or prophylaxis of such diseases which are caused in a disturbance and/or in an influence of the cyclooxygenase-2-inhibition, wherein a pharmaceutical composition comprising a cyclooxygenase-2-inhibitor according to the afore described type as active ingredient is orally administered in a daily dosage of 100 to 2000 mg, relative to the active ingredient, for an adult.

Perferably a composition is orally administered to an adult having such a concentration of said active ingredient that a daily dosage of 200 to 1000 mg is given.

If the inventive method is used for therapy and/or prophylaxis of such diseases which are caused in a disturbance and/or in an influence of the cyclooxygenase-2-inhibition a pharmaceutical composition comprising a cyclooxygenase-2-inhibitor as active ingredient is perorally administered in a daily dosage of 0.05 to 1000 mg, relative to the active ingredient, for an adult.

Preferably the inventive method is used for therapy and/or prophylaxis of ischemic diseases, senile dementia, cancer, asthma, arterial sclerosis, and/or inflammation diseases.

Depending on the concentration of the active ingredient which is to administer the inventive composition is given one time to three times each day.

DESCRIPTION OF PREFERRED EMBODIMENTS

The present invention will next be described in detail.

As mentioned above, the present invention provides a cyclooxygenase-2-inhibitor containing, as an active ingredient, a compound of formula (1). Substituents for the formula (1) compound are as follows:

$R^1$ is a hydrogen atom or an alkyl group having 1–3 carbon atoms, with hydrogen being preferred.

$R^2$ is a hydrogen atom, a hydroxyl group, or an organothiol group, such as a peptide or protein, capable of binding through its sulfur atom to the selenium atom, or $R^1$ and $R^2$ may join to each other to form a single bond.

$R^3$ is a hydrogen atom, a halogen atom, an alkyl group having 1–3 carbon atoms, an alkoxyl group having 1–3 carbon atoms, a trifluoromethyl group, or a nitro group. Among these, hydrogen is preferred.

The present invention also provides a cyclooxygenase-2-inhibitor containing, as an active ingredient, a compound of formula (2). Substituents for the formula (2) compound are as follows:

$R^2$ in the above formula (2) denotes a peptide or protein capable of binding through its own thiol group within the molecule; with regard to the protein or the peptide, any protein or peptide can be used as far as it is physiologically acceptable; however, proteins present in serum such as albumins and globulins are preferred; further, among these serum proteins, the albumins are much preferred; and among the albumins the human albumin is most preferred.

The synthesis method of compound A used in the present invention has already been disclosed in Japanese Patent Publication (*kokoku*) No. 2-38591 (i.e., Japanese Patent Application Laid-open (*kokai*) No. 57-67568). The synthesis method for compound B has also been disclosed in Japanese Patent Application Laid-open (*kokai*) No. 7-233056.

Through known formulation techniques, the compound A of the present invention can be formulated in the form of a tablet, capsule, powder, granule, syrup, or preparation for injection, along with additives such as an excipient, binder, disintegrator, and solubilizer.

Specific formulation examples will be described below.

In the case of the tablet, the following formula may be used:

| Tablet | |
|---|---:|
| compound A | 50 mg |
| carboxymethylcellulose | 25 mg |
| starch | 5 mg |
| crystalline cellulose | 40 mg |
| magnesium stearate | 2 mg |
| total | 122 mg |

Compound A, when delivered by typical oral administration or parenteral administration such as injection, manifests respective expected primary pharmacological effects. In the case of oral administration, the dosage of chemical compound A is 100–2000 mg/day, preferably 200–1000 mg/day, for an adult. The dosage can be changed, depending on the severity of the patient's symptoms.

The 2-phenylcarbamoyl-phenylselenyl derivatives of the present invention and physiologically acceptable salts thereof are administered orally or parenterally. In the case of peroral administration to adults, the dosage is usually 0.05–1000 mg/day.

Toxicity

Concerning the toxicity of compounds A and B, their LD50 values were determined through use of mice and rats. The LD50 of each compound for the mouse was not less than 6810 (mg/kg) when administered orally, and was 740 (mg/kg) when administered intraperitoneally. In the case of the rat, to reach LD50, large doses were required. These results indicate that safety levels for administration of those compounds are very high. One of the compounds, S-(2-phenylcarbamoyl-phenylselenyl)albumin, was tested for the acute toxicity. The compound was dissolved in physiological saline and was intravenously administered to mice (5 g/kg). Its LD50 was much higher than 1 g/kg, thus confirming its high safety level.

Acute Toxicity

Four Wistar strain male rats at 8 weeks of age were subjected to an acute toxicity test. S-(2- phenylcarbamoyl-phenylselenyl)albumin dissolved in physiological saline was intravenously administered (1 g/kg/3 ml), and then the rats were observed for the next twenty-four hours. Within the observation period, no particular side effect was noticed, and all rats survived healthily. Furthermore, upon much higher doses of administration to both the mouse and rat, no problematic side effect was observed.

Among the compounds, S-(2-phenylcarbamoyl-phenylselenyl)albumin is expected to achieve the most promising efficacy. Prostaglandin H2 synthesized with cyclooxygenase 2 and its metabolites, such as prostaglandin D2, E2, and F2 and thromboxane A2 and B2, are placed in the arachidonate cascade, downstream of arachidonic acid. As mentioned above, these are involved in ischemic diseases, senile dementia, cancer, asthma, arterial sclerosis, and a variety of inflammation diseases. These diseases can be treated with the 2-phenylcarbamoyl-phenylselenyl derivatives as well as with physiologically acceptable salts thereof, and excellent prognosis is expected upon their administration.

In the present invention, the 2-phenylcarbamoyl-phenylselenyl derivatives encompass compound A and compound B.

Through known formulation techniques, the 2-phenylcarbamoyl-phenylselenyl derivatives of the present invention and physiologically acceptable salts thereof can be formulated in the form of a tablet, capsule, powder, granule, syrup, or preparation for injection, along with additives such as an excipient, binder, disintegrator, and solubilizer.

The 2-phenyl-1,2-benzisoselenazol-3(2H)-one derivatives and 2-phenylcarbamoyl-phenylselenyl derivatives, both being compounds of the present invention, were tested in vitro for their inhibitory effects on cyclooxygenase 2 activity, which catalyzes synthesis of prostaglandin H2 from arachidonic acid. The results show remarkably strong inhibitory effects, which were much stronger than that of indomethacin (see Table 1).

Thus, the 2-phenyl-1,2-benzisoselenazol-3(2H)-one derivatives and 2-phenylcarbamoyl-phenylselenyl derivatives, both being related to the present invention, are most promising candidates as drugs for treatment of the above diseases that involve synthesis of prostaglandin H2 with cyclooxygenase 2.

The present invention will be described next in detail by way of experimental examples, which should not be construed as limiting the scope of the present invention.

Experimental Example 1

Arachidonic acid was used as the substrate in the present example. Ten μl of arachidonic acid was dissolved in methanol (10 mg/ml) and mixed with 5 μCi of $^{14}$C-labeled arachidonic acid; and to obtain a dried substrate, the solvent was evaporated by blowing with nitrogen gas at room temperature. Subsequently, the substrate was dissolved in 50 μl of dimethylsulfoxide (DMSO), and 10 ml of 5 mM Tris-HCl buffer (pH 8.0) containing 2 mM phenol was added to the substrate solution, followed by sonication to completely dissolve the sample. Separately, test compounds having final concentrations of 0.1–10 μM were prepared. In this experiment, a human serum albumin (HAS)—binding compound was dissolved with the above buffer, and the other compounds were dissolved with DMSO. Five μl of each compound solution was added to 5 μl of the above substrate solution, followed by mixing. The samples were then preincubated at 35° C. for about 10 min. Cyclooxygenase 2 derived from sheep placentae (Cayman Chem.) had been separately diluted 10-fold with the above buffer, and 20 μl of the enzyme solution was added to each of the above samples. The enzyme reaction was carried out at 35° C. for 30 min, and stopped by adding 0.5 ml of ice-cold ethanol to each sample. Then, to 0.9 ml of each sample, 2.0 ml of 2% acetic acid solution was added. Arachidonic acid and its metabolite prostaglandin H2 were then extracted with 3.0 ml of ethyl acetate. From each extracted sample, a 2.0-ml portion was transferred to a new test tube. The solvent was distilled off from the transferred samples under reduced pressure, and the samples were dried in vacuo. Then each dried sample was dissolved in 100 μl of methanol, out of which 5 μl was subjected to analysis by high resolution thin layer chromatography. Arachidonic acid and its metabolite prostaglandin H2 were separated by chromatography with a developing solution of chloroform, ethyl acetate, methanol, acetic acid and water in proportions of 70:30:8:1:0.5 (v/v). The chromatography plate, together with a $^{14}$C-standard substance, was exposed to an imaging plate (Fuji Film), and was analyzed with Fuji Film Bio-Image analyzer BAS-2000 to obtain an autoradiogram. By scanning of spots corresponding to the standard radioactive samples, a standard dose-response curve was plotted. Then, by use of the standard curve, each scanned value of arachidonic acid spots and prostaglandin H2 spots was converted to a amount of radiation. Indomethacin was purchased from Sigma, and PZ25 was a gift from Rhone-Poulenc Rorer. The results are shown in Table 1.

TABLE 1

| | Cyclooxygenase Inhibitor 2 | | | |
| --- | --- | --- | --- | --- |
| Dose of compound | Generated Amount of Prostaglandin H2 (%) | | | |
| (μM) | Compound A | Compound B | PZ25 | Indomethacin |
| 1 | 91.8 ± 14.3 | 78.33 ± 10.58 | N.D. | N.D. |
| 3 | 78.6 ± 5.28 | 72.13 ± 4.53* | 103.25 ± 9.29 | 95.55 ± 7.87 |
| 10 | 46.88 ± 6.49** | 35.40 ± 1.49** | 103.53 ± 11.2 | 99.45 ± 7.80 |
| 30 | 20.10 ± 1.95** | N.D. | 93.9 ± 9.06 | 96.55 ± 9.63 |
| | N.D. | N.D. | N.D. | N.D. |

ND: Not done

Significance level for p-value: *, P<0.05; **, P<0.01 (calculated by Williams-Wilcoxon test)

Compound A: 2-phenyl-1,2-benzisoselenazol-3(2H)-one

Compound B: S-(2-phenylcarbamoyl-phenylselenyl)albumin

PZ25: 2-phenyl-1,2-benzisothiazol-3(2H)-one

What is claimed is:

1. A method of inhibiting cyclooxygenase-2 in a host, which comprises administering to a host in need thereof an effective amount of a compound having the formula (1) or (1'):

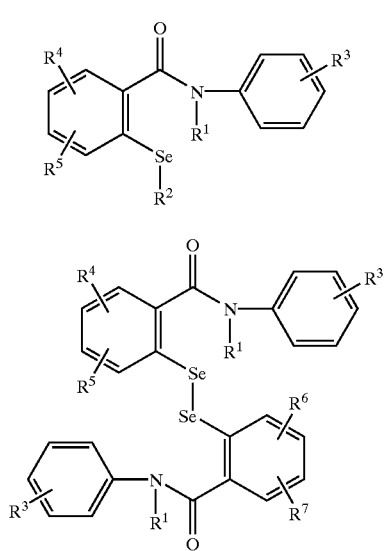

wherein $R^1$ is a hydrogen atom or an alkyl group having 1–3 carbon atoms;

$R^2$ is a hydrogen atom, a hydroxyl group, an organothiol group that is bound to the selenium atom by its sulfur atom, or $R^1$ and $R^2$ are joined to each other by a single bond;

$R^3$ is a hydrogen atom, a halogen atom, an alkyl group having 1–3 carbon atoms, an alkoxyl group having 1–3 carbon atoms, a trifluoromethyl group, or a nitro group;

$R^4$ and $R^5$ are identical to or different from each other, and each is a hydrogen atom, a halogen atom, an alkoxyl group having 1–4 carbon atoms, a trifluoromethyl group, or $R^4$ and $R^5$ are joined to each other to form a methylenedioxy group, a salt thereof, or a hydrate thereof.

2. A method as claimed in claim 1, wherein $R^2$ is an organothiol group, wherein the organothiol group is a sulfur-containing peptide, protein, or glycoprotein, the sulfur atom of which is bound to the selenium atom.

3. A method as claimed in claim 1, wherein $R^2$ is an organothiol group, wherein the organothiol group is a sulfur-containing albumin, glutathione group, or α-amino acid group, the sulfur atom of which is bound to the selenium atom.

4. A method as claimed in claim 3, wherein the albumin is human albumin.

5. A method as claimed in claim 1, which comprises administering 2-phenyl-1,2-benzisoselenazol-3(2H)-one, a salt thereof, or a hydrate thereof.

6. A method as claimed in claim 1, which comprises administering S-(2-phenylcarbamoyl-phenylselenyl)-albumin, a salt thereof, or a hydrate thereof.

* * * * *